United States Patent [19]

Kerz

[11] Patent Number: 5,550,153
[45] Date of Patent: Aug. 27, 1996

[54] METHOD FOR TREATING HEARTWORM-INFECTED CANINES

[76] Inventor: Phillip D. Kerz, Rte. 4, Box 12, Charleston, Ill. 61920

[21] Appl. No.: 338,687
[22] Filed: Nov. 14, 1994
[51] Int. Cl.⁶ .................................................. A01N 43/16
[52] U.S. Cl. ............................................................ 514/460
[58] Field of Search ............................................. 514/460

[56] References Cited

U.S. PATENT DOCUMENTS

| | | | |
|---|---|---|---|
| 4,199,569 | 4/1980 | Chabala et al. | 424/180 |
| 4,310,519 | 1/1982 | Albers-Schonberg et al. | 424/181 |
| 4,430,329 | 2/1984 | Blair | 424/181 |
| 4,853,372 | 8/1989 | Williams et al. | 514/30 |

OTHER PUBLICATIONS

Medline 92264541 (Apr. 1992).
Medline 92221562 (Feb. 1992).
Medline Abstract 92152543 (Nov. 1991).
Clark et al. (1992), Efficacy of Ivermectin and Pyrantel Pamoate Combined in a Chewable Formulation Against Heartworm, Hookworm, and Ascarid Infections in Dogs, *Am J Vet Res* 53:517–520.
Paul et al. (1991), Efficacy of Ivermectin Chewable Tablets and Two New Ivermectin Tablet Formulation Against *Dirofilaria Immitis* Larvae in Dogs, *Am J Vet Res* 52:1922–23.
Nolan et al. (1992), Efficacy of an Ivermectin/Pyrantel Pamoate Chewable Formulation Against the Canine Hookworms, *Uncinaria Stenocephala* and *Ancylostoma Caninum*, *Veterinary Parasitology* 41:121–5.
Magazine advertisement for Heartgard 30® Plus, 1995.
American Heartworm Society Bulletin, vol. 10, No. 3 (Sep., 1984).
American Heartworm Society Bulletin, vol. 19, No. 2 (Jun., 1993).
American Heartworm Society Bulletin, vol. 20, No. 3 (Sep., 1993).
Two–Day Treatment With Thiacetarsimide For Canine Heartworm Disease, R. F. Jackson, J.A.V.M.A., vol. 142, No. 1, pp. 23–5 1981.
Thiacetarsimide Re–Evaluation, Jackson and Otto, Proceedings of 1980 Heartworm Symposium, pp. 137–140 and 153–156.
Heartworm Caval Syndrome, Atkins, Current Veterinary Therapy, pp. 721–5 1992.

*Primary Examiner*—Paul J. Killos
*Attorney, Agent, or Firm*—Howell & Haferkamp, L.C.

[57] ABSTRACT

Successful treatment of adult canine heartworm disease (*dirofilaria immitis*) has been very difficult to achieve. Presently, only one drug is approved for this application by the Counsel of the American Veterinary Medical Association and the Executive Committee of the American Heartworm Society. This drug is thiacetarsimide, an intravenously administered and arsenic-derived compound which has proven moderately efficacious at destroying adult heartworms which are responsible for producing the adverse physiological effects that characterize dirofilaria immitis. Thiacetarsimide is known to induce a host of possible adverse side-effects including anaphylactic shock, liver disease, kidney disease and patient mortality. It has been found that ivermectin, one of a broad class of antiparasiticidal avermectins, is efficacious in destroying both adult and immature heartworms in canines when administered in an effective dose. As compared to thiacetarsimide-based regimes, methods employing ivermectin are efficacious yet less expensive and more convenient for treating canines afflicted with adult heartworms.

17 Claims, No Drawings

METHOD FOR TREATING HEARTWORM-INFECTED CANINES

BACKGROUND OF THE INVENTION

This invention relates generally to a non-invasive method for treating dirofilaria immitis in canines and, more particularly, to a method for treating that stage of the disease caused by adult heartworms. Still further, the invention employs ivermectin—a composition hereto-fore unknown in the primary treatment of adult heartworms.

Heartworms are commonly found to reside in the right ventricle of a dog's heart and the adjacent blood vessels. Adult heartworms cause inflammation of the walls of the arteries in the lungs, obstruct blood vessels and interfere with the blood supply to vital organs. Common symptoms of adult heartworm disease in canines include low-grade nocturnal cough, distension of the limbs and lower abdomen and lethargy. Left Untreated, heartworm parasites can result in the death of the host canine and can be infectiously transmitted to other canines by way of numerous mosquito species which function as an intermediate host.

Dirofilaria immitis, the disease caused by parasitic adult heartworms in canines, is characterized by several developmental stages. Specifically, microfilariae are known to be deposited by female heartworms into the bloodstream of canines. The microfilariae develop further once ingested by a mosquito which functions as an intermediate host. Within the mosquito, microfilariae develop into infective larvae which, once a dog is bitten by the mosquito, migrate to the dog's heart where maturation into adult worms occurs.

As reported as early as January, 1963, the only known pathologic changes in canines based upon heartworm disease result from the direct or indirect effects of adult heartworms. No significant damage is done by either the microfilariae or the developing larvae. (See Jackson, Journal of the American Veterinary Medical Association 142, pages 23–26 (1963)). Accordingly, efforts in the treatment of heartworms in canines, since that time, have largely been directed toward destruction of the adult heartworm.

Destruction of the adult worm has been accomplished surgically and by chemotherapy. Beginning in the 1940's and continuing into the early 1960's several open-chest surgical techniques were developed and practiced for removing worms from the right ventricle and adjacent arteries. Surgical removal of worms through the animal's jugular vein was also practiced for some time and remains the recommended procedure for eliminating adult worms in confirmed cases of heartworm caval syndrome. With this exception, however, surgical treatments have yielded to chemotherapies because they proved expensive, risky (mortality rates in excess of 10% were reported) and, most importantly, non-efficacious. In fact, chemotherapy was regularly prescribed following surgery.

Fuadin®, a trivalent antimonial agent, was an early product used to chemically treat heartworm in canines. It was determined, however, that while this drug proved effective at sterilizing female worms—thereby preventing the production of microfilariae, it was ineffective at destroying adult worms. This factor, in conjunction with demonstrated toxicity, caused this drug to fall out of common use.

Beginning in about 1970, levamisole became a drug thought to possess an adulticidal character. Extensive controlled studies, however, demonstrated that the adulticidal activity of the composition was widely inconsistent. On this basis, the only recommended use of levamisole in the treatment of dirofilaria immitis is as a microfilaricide. (See Levamisole in Dirofilariasis in Dogs, J.A.V.M.A. 176 (10 part 2), 1170–1172 (1980)).

Occurring simultaneously with the development of the surgical and chemical treatments thus discussed, was the development of a chemotherapy treatment with demonstrated and comparatively efficacious adulticidal character. Thiacetarsimide, a substituted phenyl arsenoxide, is available under several branded names including Caparsolate Sodium® and Filaramide®. In continuing studies dating back to 1947, thiacetarsimide has been shown to kill effective numbers of adult worms in canines when administered at a variety of dosage and frequency variables. Through continuous experimentation, the once standard fifteen (15) day treatment regimen which involved a once daily administration of 0.1 cc of a 1% thiacetarsimide solution per pound of canine body weight has now been supplanted by a regimen of twice daily administrations of the same solution (1% thiacetarsimide) in individual doses of 0.1 ml per pound of canine weight for two consecutive days. Despite established side-effects including anaphylactic shock and periodic mortality as well as known hepatotoxic and nephrotoxic potentials, this protocol continues to date as the only approved treatment of dirofilaria immitis due to its consistent adulticidal efficacy of greater than about 70 per cent. (See R. F. Jackson, et al., Proceedings of the Heartworm Symposium (1980), pages 137–138 and 153–156, Otto, Editor, Veterinary Medicine Publishing Company (1981) and Clarke E. Atkins, Heartworm Caval Syndrome, Current Veterinary Therapy XI—Small Animal Practice, pg. 725 W. B. Saunders Co., (1992)).

Recently, ivermectin and other avermectin compounds have developed as a group of antiparasiticidal compounds of microbial origin. Avermectins, generally, are disclosed in U.S. Pat. No. 4,310,519 to Albers-Schonberg, et. al. Therein, the applicability of this broad class of compounds is intimated in connection with canine heartworm disease and it is suggested at col. 14, lines 19–23 that a mixed concentrate of the compounds proved successful in treating microfilariae in a single dog. Significantly, however, no disclosure is made regarding the applicability of the avermectins, generally, or ivermectin, specifically, in the eradication of adult canine heartworms.

Ivermectin is disclosed in U.S. Pat. No. 4,199,569 to Chabala, et. al. As do Albers-Schonberg, et. al., this patent too only hints at the possible application of the avermectins and, more particularly, ivermectin, in treating heartworm disease in canines. Further, it too fails to disclose any method for treating adult heartworm-afflicted canines and, in fact, provides no disclosure regarding which aspect or stage of the disease may respond to any of the compounds therein disclosed.

More recently, and with reference to U.S. Pat. No. 4,430,329 to Blair, ivermectin has been more particularly disclosed in conjunction with the treatment of heartworm-afflicted canines. Specifically, a protocol has been disclosed which involves the initial, primary treatment of dirofilaria immitis with thiacetarsimide conventionally followed three to six weeks thereafter by treatment with ivermectin. While it is expressly noted at col. 2, lines 13–15 that "Ivermectin itself has no demonstrable activity against adult canine heartworm . . . ", and again at col. 4, line 5 that " . . . another drug [ivermectin] which has no adulticidal activity . . . ", ivermectin is therein disclosed and described as having a potentiating or synergistic effect on thiacetarsimide which, discretely, is known to have some activity against the adult heartworm. As such, it is believed that Blair teaches away from the method of the present invention which in no way employs thiacetarsimide.

U.S. Pat. No. 4,853,372 to Williams, et. al. discloses the most recent application of ivermectin as an antiparasiticidal composition—of which this inventor is aware. Specifically, this patent discloses an injectable ivermectin formulation which has demonstrated efficacy in treating ectoparasites such as ticks in cattle. In examples 1 and 2, at columns 3 and 4 respectively, two formulations are described. The first involves 1.0% weight by volume ivermectin in a solution of glycerol formal and propylene glycol and the second contains an equal concentration of ivermectin in a solution of water and propylene glycol. As with the other references hereto discussed, however, this patent also lacks any disclosure relating to the use of ivermectin as an adulticidal composition in the treatment of dirofilaria immitis.

The foregoing establishes that considerable, albeit unsuccessful efforts have been expended in this art to develop an effective, safe and convenient method for treating adult heartworms in canines. These efforts notwithstanding, the only known and approved modality existing presently requires the administration of thiacetarsimide, an arsenic-derived compound having a vast array of known side-effects and a demonstrated incidence of patient mortality. Thus, the art has lacked a safe, efficacious, convenient and comparably inexpensive method for killing adult heartworms in canines without using thiacetarsimide. The invention disclosed and claimed herein achieves these advantages in a manner not revealed by the prior art.

SUMMARY OF THE INVENTION

The present invention provides an efficacious chemotherapeutic method for destroying adult, symptom-producing heartworms in canines. Dirofilaria immitis, is the deleterious and sometimes fatal parasitic disease caused by heartworms in canines. It is characterized by arterial wall inflammation, limb and lower abdomen distension and lethargy in the afflicted host animal. Worms, in various stages of larval development, reside in the canine's heart and surrounding blood vessels and, by virtue of their parasitic activity, cause the disease. While several modalities are known for efficaciously destroying immature worms, the destruction of adult worms, until now, has always required administration of thiacetarsimide.

Thiacetarsimide is an arsenic-derived compound and, although it is known to have a moderate to good adulticidal character, is also associated with significant adverse side-effects including hepatotoxic and nephrotoxic potentials as well as a mortality incidence. Additionally, thiacetarsimide-based treatments are administered intravenously and therefore are relatively expensive and inconvenient for both the patient and its owner.

Ivermectin, an avermectin compound of microbial origin, is a known microfilaricide and apparent potentiator of the adulticidal character of thiacetarsimide when administered in conjunction therewith. The present invention provides an efficacious and heretofore unknown and unexpected method for treating canines afflicted with adult heartworms with ivermectin discretely such that thiacetarsimide administration is wholly eliminated.

The treatment method of the present invention involves administering a preparation containing a 1% ivermectin composition at a prescribed dosage on an outpatient or owner-administered basis over a period of between six to twelve consecutive months. Efficacy of the method is confirmed by an antigenic testing procedure particularly known for its high specificity to dirofilaria immitis.

The ivermectin preparation employed in the present invention is considerably less toxic than thiacetarsimide and, excepting the possibility of inducing shock following the first or second administrations, is not known to produce any of the other adverse side-effects associated with thiacetarsimide.

While the principal advantages and features of the present invention have been described above, a more complete and thorough understanding of the invention may be attained by referring to the more detailed description of the preferred embodiment which follows.

DETAILED DESCRIPTION OF THE PREFERRED EMBODIMENT

The present invention relates to an improved method for treating canines afflicted with dirofilaria immitis by employing an ivermectin preparation. The method of the present invention has particular utility in efficaciously destroying adult canine heartworms which are primarily responsible for the adverse physiological consequences caused by the disease in canines. Adult worms, together with other worms in various stages of larval development, reside in and around the canine's heart muscle. When adult worms exist in sufficient number, they create lesions and occlude and interfere with the proper function of vital heart and related arterial and venous structures. Further, dirofilaria immitis is known to cause damage to vital organs such as the kidneys and liver.

The method of the present invention is also efficacious in destroying developing microfilariae produced by adult female filariae. This is significant because, when microfilariae are ingested by intermediate-host mosquitoes, they develop into infectious larvae. Thereafter, the infectious larvae may be deposited into the blood stream of an uninfected dog once the uninfected dog is bitten by a carrier mosquito. From the blood stream, the infectious larvae migrate to the vicinity of the newly infected animal's heart where they reside and mature into disease-causing adult worms. Accordingly, the method of the present invention is efficacious both in arresting adult-stage dirofilaria immitis and in controlling the spread of the disease by microfilariae.

The prophylactic or microfilaricidal effect of ivermectin in heartworm-afflicted canines is a concomitant aspect of the present invention. Further, and as previously indicated, it has been reported on as a separate phenomenon discrete from ivermectin's heretofore unknown adulticidal character.

For example, as noted in the patent to Blair, "[i]vermectin and other related avermectin compounds . . . have been found to be very active against the microfilarial stage of canine heartworm." Further, as discussed under the heading "ELIMINATION OF MICROFILARIAE" in a recent statement of American Heartworm Society recommended procedures, it is noted that, while the use of ivermectin as a microfilaricide in canines is an "extra-label" application, microfilariae are most efficiently eliminated with an ivermectin microfilariicidal dose of 50 mcg/kg. (See American Heartworm Society Recommended Procedures For The Diagnosis and Management of Heartworm (*Dirofilaria Immitis*) Infection, presented at the 1992 triennial symposium of the American Heartworm Society).

The adulticidal character of ivermectin has heretofore been unknown. Moreover, based upon earlier work conducted in the field, the avermectins and ivermectin, specifically, have been regarded as having no adulticidal effect. However, and despite the prior art that teaches away from the present invention, it has been found that the administration of a preparation containing an ivermectin composition, by itself, is efficacious in eliminating adult heartworms in canines.

Ivermectin was first marketed by Merck & Co., Inc. as an equine injectable dewormer under the tradename Eqvalan. Eqvalan has since been withdrawn from the market and ivermectin is now available as an injectable cattle and reindeer de-wormer under the tradename Ivomec® The principal difference between the formulations appears to reside in their relative concentration. Whereas Eqvalan was a 2% ivermectin solution (20 mg/cc), Ivomec® is a 1% (10mg/cc) solution.

As more specifically described by its manufacturer, Ivomec® is a clear, ready-to-use, sterile solution containing 1% ivermectin, 40% glycerol formal, and propylene glycol, q.s. ad 100%. When administered to cattle and reindeer in the recommended dose level of 200 mcg. ivermectin/kg. of body weight given subcutaneously at the rate of 1 ml./110 lbs. it is believed to be highly effective at destroying gastrointestinal roundworms, lungworms, grubs, sucking lice and mange mites. The manufacturer's cautionary label indications state that Ivomec® has been developed specifically for use in cattle and reindeer only and that severe adverse reactions, including fatalities in dogs, may result if the product is used in other animal species.

When Ivomec® is used as an "extra-label" microfilaricide in canines, the 1% solution is mixed with U.S.P. propylene glycol in a ratio of 1 ml. of Ivomec® to 9 ml. propylene glycol and administered orally in a dose of 1 ml./44 lbs. canine body weight. The regimen for treating microfilariae with this ivermectin composition requires treating the dog initially with the adulticidal thiacetarsimide composition followed several weeks thereafter with concentration microfilariae testing. If the results are negative, the animal may be started on the ivermectin prophylactic regimen which is administered in tablet form once per month at a dose of 6 mcg./kg. or 2.72 mcg./lb. of animal weight. Many veterinarians, however, conventionally insist upon two consecutive negative concentration test results prior to initiating the prophylactic regimen in a dog that is known to have had adult worms.

If positive test results are obtained, the dog is administered a single morning dose of the ivermectin/propylene glycol solution at the recommended dose of 0.05 mg./kg. or 1 ml./44 lbs. body weight and the patient is observed throughout the balance of the day. The possibility of the onset of anaphylactic shock exists in about 2% of the dogs receiving this treatment as reported. Because a substantially direct relationship exists between the concentration of circulating microfilariae in the canine (as indicated by the concentration test) and the likelihood of shock onset, however, this complication is largely predictable and can be brought under control using efficacious cortico-steroid and antihistamine compositions.

Following microfilarial treatment, as above described, the dog is released to its owner and re-evaluated in approximately three weeks, whereupon, a subsequent microfilariae concentration test is again performed. Where the results are positive, the above regimen is repeated. If the test proves negative, however, the canine can be started on the prophylactic ivermectin formulation.

EXAMPLE

In Table 1, below, the results of the experimental use of ivermectin as an adulticidal heartworm composition are reported. As clearly shown, five canines have been successfully treated for dirofilaria immitis using a heretofore unknown regimen consisting only of a monthly administration of ivermectin.

TABLE 1

| CASE | DATE DIAGNOSED | DATE(S) OF INITIAL TREATMENT | DATE(S) RE-TESTED | TEST RESULT(S) |
|---|---|---|---|---|
| 1 | 12/04/87 | 04/29/88 | 12/21/89 | Negative |
| 2 | 09/07/91 | 09/07/91 | 10/13/92 | Negative |
| 3 | 02/04/92 | 03/10/92 | 02/08/93 | Positive |
|   |          | 02/10/93 | 08/24/93 | Negative |
| 4 | 10/12/92 | 10/13/92 | 07/29/93 | Negative |
| 5 | 05/25/93 | 05/25/93 | 05/24/94 | Negative |
| 6 | 02/04/93 | 02/04/93 | 02/26/94 | Positive |
| 7 | 08/09/93 | 08/09/93 | 06/08/94 | Positive |
| 8 | 04/17/93 | 04/26/93 | *N/A | *N/A |
| 9 | 05/09/94 | 05/09/94 | *N/A | *N/A |

*Information not available at time of application

The case studies reported above reflect the results of testing performed on dogs of various ages, sizes and breeds. The same ivermectin composition, however, was administered to all of the dogs that participated in the study. The composition can be administered via any standard route of drug administration including the oral and parenteral routes. The preferred route of administration, however, is oral and, as employed in the study, the composition comprised a 1% solution of ivermectin available from Merck & Co. as Ivomec®. The 1% solution was mixed with a pharmaceutically suitable carrier to form a preparation suitable for oral administration despite that, as explained above, the 1% Ivomec® solution is intended for parenteral administration.

Preferably, the pharmaceutically suitable carrier is propylene glycol which is preferably mixed with 1% ivermectin in a by weight ratio of nine parts propylene glycol to every one part of ivermectin to form a curative solution. The curative solution can be administered orally in an effective dose within the range of about 18–30 mcg./lb. of animal body weight. More preferably, the dose is within the range of about 20–24 mcg./lb. and, most preferably, the effective dose is about 23 mcg./lb. of animal body weight. This dose is substantially equivalent to the 50 mcg./kg. or 22.6 mcg./lb. dose that has been used in conjunction with thiacetarsimide to treat microfilaria. As compared to the prophylactic ivermectin dose (2.72 mcg./lb.) contained in products such as Heartguard 30®, however, the ivermectin dose administered in the study was approximately eight times more concentrated.

Each dog participating in the study was diagnosed with dirofilaria immitis using an immunodiagnostic test for canine heartworm antigen. A number of commercially available tests of this nature are available and these tests have proven highly sensitive and specific for detecting antigens produced by the presence of three or more adult female heartworms. The particular test used in this study was the CITE® brand test which is produced by Idexx Laboratories. A positive CITE® test indicates the presence of three or more adult female heartworms while a negative test result indicates that fewer than three, if any, adult female worms exist in the animal. The reliability of the CITE® brand antigen-identifying test has clearly been shown to be nearly 100%.

In each of the cases reported above, the owner of the animal was advised of the experimental nature of the proposed treatment and was required to sign a liability release. The initial ivermectin administration was performed under clinical conditions so that the animal could be observed for the onset of any adverse side-effects. Subsequent, monthly administrations were to be performed by the pet owner in accordance with veterinarian instruction. Basically, each pet owner was provided with an oral syringe and advised regarding the effective dose to be administered to his/her dog based upon the animal's body weight. Instruction was given to administer the ivermectin in the proper dose once per month for an initial period of six months. The owners were advised that the ivermectin could either be injected directly into the animal's mouth or injected into and mixed with its food ration. At the end of this period, the pet owner was requested to return to the clinic in order that the animal could be re-tested for heartworm antigen.

Because all but the first of the monthly treatments were administered by the pet owner, the integrity of the experimental results directly depended upon pet owner compliance with the treatment regimen. For example, in Case 3 above the pet owner admitted that the ivermectin treatment was administered sporadically during the eleven month period commencing with the first treatment in March, 1992 and ending when the dog was re-tested in February, 1993. Thus, it was not surprising that heartworm antigen was detected during re-testing. Six months later, however, the same dog was again tested and found to be negative for antigen. At the time of the retest, the pet owner admitted that strict adherence had been kept to the treatment regimen during the six months. Similar pet owner non-adherence to the treatment protocol are believed to account for the positive re-test results observed in cases 6 and 7. The animals which are the subject of cases 8 and 9 have not been re-tested at the time of this disclosure.

In view of the results thus compiled, it can be seen that an effective treatment has been identified which simultaneously eliminates microfilaria and adult worms in dogs. By comparison to the treatment of dirofilaria immitis using conventional intravenous administration of thiacetarsimide, the treatment of the present invention is safer, more effective and considerably less expensive.

No dogs have died during the experimentation and in only two cases (7 and 9) has treatment been required for symptoms of shock following initial treatment. It is believed that ivermectin, when administered in the dose disclosed herein, is safe for dogs. Thus, as reflected in Table 1, the effective eradication of adult heartworms in canines may be achieved in as short a period as six months following diagnosis. Further, it ismbelieved that puppies can be started in treatment at about six weeks of age and continued thereafter monthly conceivably for the balance of their life. If the animal receives its dose of ivermectin regularly, it is believed that it may never again need to be re-tested for heartworm antigen. This is due to the known developmental life cycle of heartworms.

While the present invention has been described by reference to specific embodiments, it should be understood that modifications and variations of the invention may be constructed without departing from the scope of the invention as defined in the following claims.

What is claimed is:

1. A method for killing adult heartworms in a canine comprising administering to the canine a series of effective doses of an avermectin composition.

2. The method of claim 1, wherein said avermectin composition is ivermectin.

3. The method of claim 2, wherein said ivermectin is administered orally.

4. The method of claim 3, wherein said effective dose is within the range of about 18 mcg./lb. to about 30 mcg./lb. of canine body weight.

5. The method of claim 2, wherein said ivermectin composition comprises a 1% solution in a pharmaceutically suitable carrier.

6. The method of claim 2, wherein the step of administering said ivermectin involves the oral administration of said composition once per month.

7. The method of claim 2, wherein said ivermectin composition comprises a 1% solution in a pharmaceutically suitable carrier and is administered orally once per month.

8. A method for killing adult heartworms in a canine, comprising the steps of:
    administering an effective, oral dose of an avermectin composition; and
    readministering said composition at intervals of approximately thirty days at least until the adult heartworms are killed.

9. The method of claim 8, wherein in the steps of administering and readministering, said composition is a 1% solution of ivermectin in a pharmaceutically suitable carrier.

10. The method of claim 8, further comprising the step of testing said canine for adult heartworms between readministrations of said composition.

11. The method of claim 8, wherein said avermectin composition comprises a solution of 1% ivermectin in a pharmaceutically suitable carrier and said dose is about 23 mcg./kg. of canine body weight.

12. The method of claim 11, further comprising the step of testing said canine for adult heartworms between readministrations of said composition.

13. A method for simultaneously killing adult heartworms and microfilaria in a canine comprising the steps of:
    administering an effective, oral dose of an avermectin composition; and
    readministering said composition at intervals of approximately thirty days at least until the adult heartworms and microfilaria are killed.

14. The method of claim 13, wherein in the steps of administering and readministering, said composition is a 1% solution of ivermectin in a pharmaceutically suitable carrier.

15. The method of claim 13, further comprising the step of testing said canine for adult heartworms and microfilaria between readministrations of said composition.

16. The method of claim 13, wherein said avermectin composition is a solution of 1% ivermectin in a pharmaceutically suitable carrier and said dose is about 23 mcg./kg. of canine body weight.

17. The method of claim 16, further comprising the step of testing said canine for adult heartworms and microfilaria between readministrations of said composition.

* * * * *